US009863932B2

United States Patent
Sano et al.

(10) Patent No.: US 9,863,932 B2
(45) Date of Patent: Jan. 9, 2018

(54) GAS MEASUREMENT APPARATUS, GAS MEASUREMENT SYSTEM, GAS MEASUREMENT METHOD, AND GAS MEASUREMENT PROGRAM

(71) Applicant: TANITA CORPORATION, Tokyo (JP)

(72) Inventors: Ayumi Sano, Tokyo (JP); Naotaka Minagawa, Tokyo (JP); Miyuki Kodama, Tokyo (JP); Yasuhiro Kasahara, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 184 days.

(21) Appl. No.: 14/856,024

(22) Filed: Sep. 16, 2015

(65) Prior Publication Data
US 2016/0097761 A1    Apr. 7, 2016

(30) Foreign Application Priority Data

Oct. 3, 2014  (JP) ................. 2014-205085

(51) Int. Cl.
*G01N 33/49*  (2006.01)
*G01N 33/497*  (2006.01)
*G01N 33/00*  (2006.01)

(52) U.S. Cl.
CPC ....... *G01N 33/497* (2013.01); *G01N 33/0031* (2013.01); *G01N 2033/4975* (2013.01)

(58) Field of Classification Search
CPC .. G01D 11/245; G01D 11/24; G01N 33/4972; G01N 33/497; G01N 1/22;
(Continued)

(56) References Cited

U.S. PATENT DOCUMENTS 4,749,553 A * 6/1988 Lopez ................ G01N 33/4972
180/272
5,826,577 A * 10/1998 Perroz, Jr. ............. A61B 5/097
600/532
(Continued)

FOREIGN PATENT DOCUMENTS

EP    2634567 A1    9/2013
EP    2878949 A1    6/2015
(Continued)

OTHER PUBLICATIONS

Communication dated Feb. 3, 2016 from the European Patent Office issued in corresponding Application No. 15185455.1.

*Primary Examiner* — David A Rogers
(74) *Attorney, Agent, or Firm* — Sughrue Mion, PLLC

(57) ABSTRACT

A gas measurement apparatus of the present invention includes a gas sensor and is capable of being in any one of an open state in which the gas sensor is connected to an outside air and a closed state in which the gas sensor is cut off from an outside air. The gas measurement apparatus includes: an acquisition unit; and a determination unit. The acquisition unit acquires a detection value of the gas sensor in the open state and a detection value of the gas sensor in the closed state. The determination unit compares the detection value of the gas sensor acquired in the open state and the detection value of the gas sensor acquired in the closed state to thereby determine the state of the gas sensor.

13 Claims, 10 Drawing Sheets

(58) Field of Classification Search
CPC ......... G01N 1/2273; G01N 2001/2244; G01N 2015/0046; G01N 2033/4975; G01N 2201/022; G01N 33/64
See application file for complete search history.

(56) References Cited

U.S. PATENT DOCUMENTS

| | | | | |
|---|---|---|---|---|
| 6,177,051 | B1 * | 1/2001 | Kimelman | G01N 33/4972 422/413 |
| 6,565,808 | B2 * | 5/2003 | Hudak | B01L 3/5023 422/411 |
| D602,384 | S * | 10/2009 | Samborn | D10/81 |
| 8,631,716 | B2 * | 1/2014 | Bernard | C12M 23/48 73/431 |
| D731,341 | S * | 6/2015 | Kobayakawa | D10/81 |
| 9,297,674 | B2 * | 3/2016 | Tanizaki | G01N 33/48757 |
| 2001/0037070 | A1 * | 11/2001 | Cranley | A61B 5/00 600/532 |
| 2007/0034028 | A1 * | 2/2007 | Tottewitz | G01N 27/283 73/866.5 |
| 2007/0078322 | A1 * | 4/2007 | Stafford | A61B 5/14532 600/347 |
| 2013/0279097 | A1 * | 10/2013 | Jacobi | H02G 3/12 361/679.01 |
| 2014/0165697 | A1 * | 6/2014 | Mochizuki | G01N 33/4972 73/23.3 |
| 2015/0047431 | A1 * | 2/2015 | Tanizaki | G01N 33/48757 73/431 |
| 2015/0124258 | A1 * | 5/2015 | Amako | G01N 21/658 356/445 |
| 2015/0377868 | A1 * | 12/2015 | Cooper | G01N 21/6428 436/128 |
| 2016/0101249 | A1 * | 4/2016 | Djupesland | A61M 11/02 128/200.23 |
| 2016/0116405 | A1 * | 4/2016 | Bertaux | G01N 15/0227 356/338 |

FOREIGN PATENT DOCUMENTS

| | | |
|---|---|---|
| GB | 2435099 A | 8/2007 |
| JP | 11-160266 A | 6/1999 |
| JP | 2010-25718 A | 2/2010 |
| JP | 2012-47711 A | 3/2012 |
| WO | 2014/143175 A1 | 9/2014 |

* cited by examiner

GAS MEASUREMENT APPARATUS, GAS MEASUREMENT SYSTEM, GAS MEASUREMENT METHOD, AND GAS MEASUREMENT PROGRAM

CROSS-REFERENCE TO RELATED APPLICATIONS

Priority is claimed on Japanese Patent Application No. 2014-205085, filed on Oct. 3, 2014, the contents of which are incorporated herein by reference.

BACKGROUND

Field of the Invention

The present invention relates to a gas measurement apparatus, a gas measurement system, a gas measurement method, and a gas measurement program.

Background

In the related art, gas measurement apparatuses or gas measurement systems are known that determine the state of a gas sensor based on a measurement result of two gas sensors of the same kind (for example, refer to Japanese Patent Application, Publication No. H11-160266 and Japanese Patent Application, Publication No. 2012-47711).

SUMMARY

However, in gas measurement apparatuses or gas measurement systems of the related art, there are cases in which the state of the gas measurement apparatus cannot be accurately determined since the measurement result of two gas sensors of the same kind is used.

An object of an aspect of the present invention is to provide a gas measurement apparatus, a gas measurement system, a gas measurement method, and a gas measurement program capable of accurately determining the state of a gas measurement apparatus.

An aspect of the present invention is a gas measurement apparatus that includes a gas sensor and is capable of being in any one of an open state in which the gas sensor is connected to an outside air and a closed state in which the gas sensor is cut off from the outside air, the gas measurement apparatus including: an acquisition unit; and a determination unit, wherein the acquisition unit acquires a detection value of the gas sensor in the open state and a detection value of the gas sensor in the closed state, and the determination unit compares the detection value of the gas sensor acquired in the open state and the detection value of the gas sensor acquired in the closed state to thereby determine the state of the gas sensor.

According to an aspect of the present invention, it is possible to accurately determine the state of a gas measurement apparatus.

DESCRIPTION OF THE EMBODIMENTS

First Embodiment

Hereinafter, a gas measurement apparatus (an apparatus for measuring a specific gas component in the breath of a user) according to an embodiment of the present invention is described with reference to the drawings. This embodiment is described using an example in which a semiconductor gas sensor unit (first gas sensor unit) 60 is embedded in a gas measurement apparatus; however, as described later, the semiconductor gas sensor unit 60 may be a separate terminal from a gas measurement apparatus. Further, if necessary, an XYZ coordinate system is used for diagramatic representation and explanation. The (A) states of FIG. 1 and FIG. 2 indicate an open state of a gas measurement apparatus 1. The (B) states of FIG. 1 and FIG. 2 indicate a closed state of the gas measurement apparatus 1.

Figure 1:
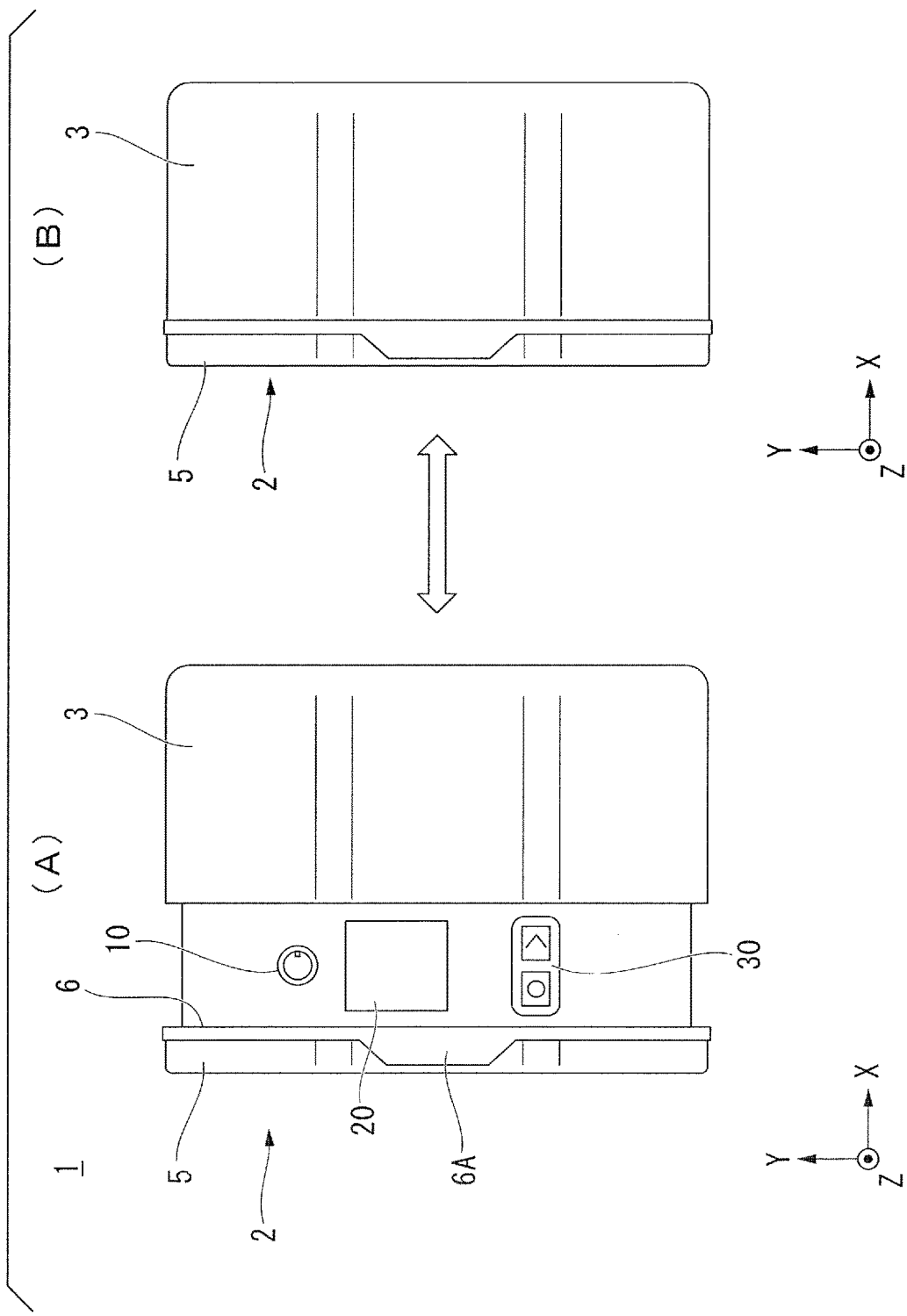
FIG. 1 is an external configuration view of a gas measurement apparatus seen from the front side.

FIG. 1 is an external configuration view of the gas measurement apparatus 1 seen from the front side. The gas measurement apparatus 1 includes a holding structure that holds a cover unit 3 to be in any one of an open state and a closed state by an operation to slide the cover unit 3 in the X direction in FIG. 1 by an operator.

The gas measurement apparatus 1 includes a body unit 2 and the cover unit 3 that covers part of the body unit 2 in the closed state. A portion in a first surface of the body unit 2, which is exposed only in the open state, is provided with a delivery port 10, a display unit 20, and an operation unit 30.

An attachable and detachable attachment 12 (shown in FIG. 3) having a hollow structure is attached to the delivery port 10 in the open state in a state where the attachment 12 is inserted in the delivery port 10. Further, a straw (not shown) is provided on the attachment 12. The breath of the user is delivered to the delivery port 10 through the straw and the attachment 12. The attachment 12 may have a configuration in which the straw is not provided, and the breath of the user may be delivered to the delivery port 10 through the attachment 12. Further, the delivery port 10 may have a configuration in which the attachment 12 is not attached to the delivery port 10, and the breath of the user may be delivered directly to the delivery port 10 without the attachment 12.

The display unit 20 is, for example, a display device such as a liquid crystal display device or an organic electroluminescence (EL) display device. The content of display of the display unit 20 is determined by a CPU 90 described later. The display unit 20 displays a variety of information for the user by a setting screen, a screen showing a measurement result, and the like. The operation unit 30 accepts a variety of operations (on/off of the power, input of user information or the like, instruction of measurement start, scroll of the screen, and the like) by the user. The content of operation applied on the operation unit 30 is output to the CPU 90 described later.

Further, a base unit 5 is formed on the body unit 2 of the gas measurement apparatus 1, the base unit 5 being formed to have a surface form that is consecutive to the cover unit 3 in the closed state. A member 6 that has a form corresponding to an end portion of the cover unit 3 and that comes into contact with the cover unit 3 in the closed state for improving airtightness is attached to an end portion of the base unit 5 that comes into contact with the cover unit 3. The member 6 is formed of, for example, an elastic material such as a rubber (for example, a silicon rubber) and an elastomer. A knob unit 6A is provided on the member 6 at a position close to the central portion of the member 6 with respect to the Y direction in FIG. 1 such that the user can easily perform an open operation. The knob unit 6A has a tilt such that a portion of the knob unit 6A is positioned further in the +Z direction as the portion of the knob unit 6A is positioned further in the −X direction in FIG. 1.

Figure 2:
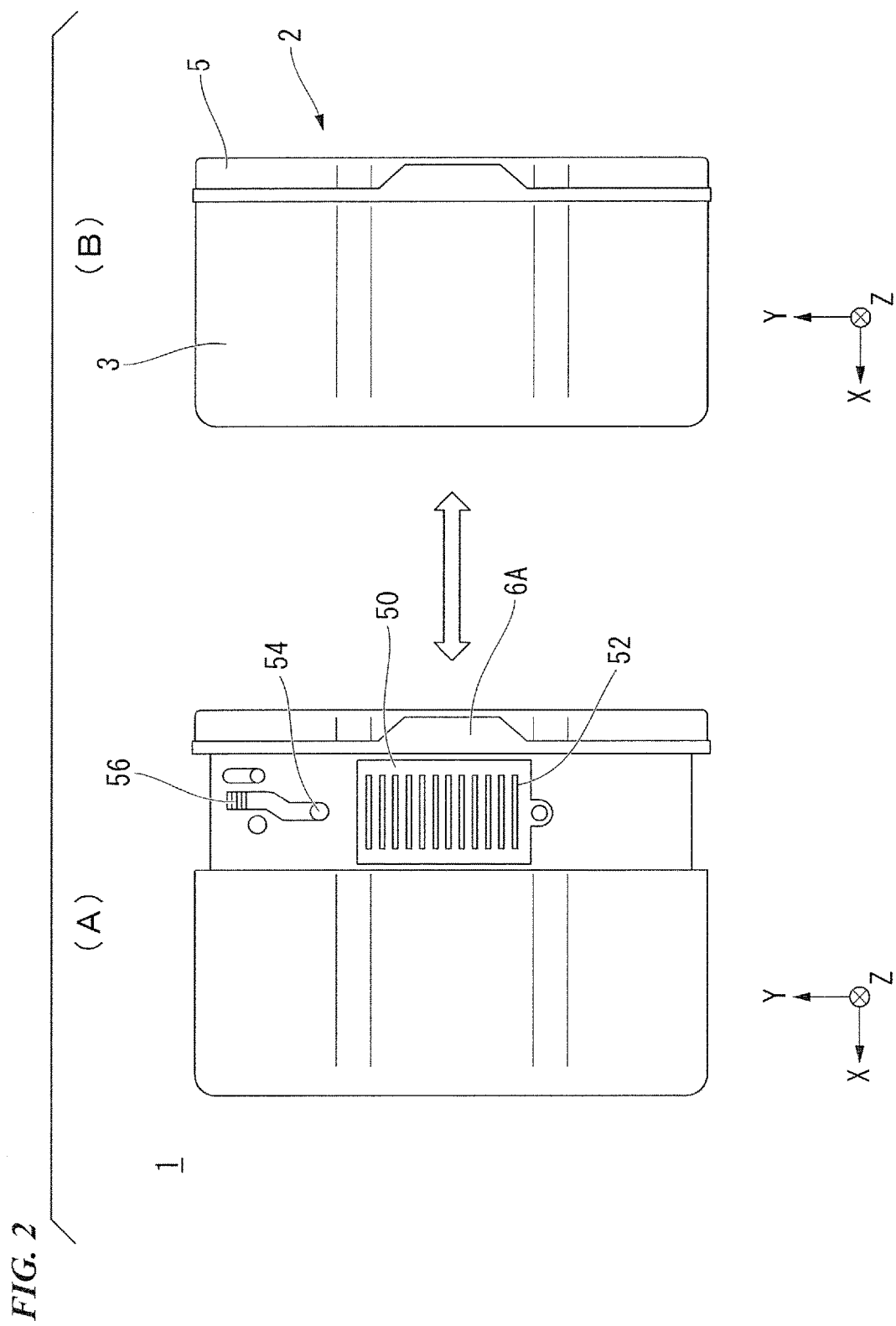
FIG. 2 is an external configuration view of the gas measurement apparatus seen from the rear side.

FIG. 2 is an external configuration view of the gas measurement apparatus 1 seen from the rear side. A portion in a second surface of the body unit 2, which is exposed outside only in the open state, is provided with an absorbent housing unit 50, a hole section 52, a hole section 54, and a hole section 56. In FIG. 2, the knob unit 6A has a tilt such that a portion of the knob unit 6A is positioned further in the −Z direction as the portion of the knob unit 6A is positioned further in the −X direction in FIG. 2.

The absorbent housing unit 50 houses a gas absorbent such as activated carbon within the absorbent housing unit 50. In the closed state of the gas measurement apparatus 1, a space that houses activated carbon is connected to a space in which a semiconductor gas sensor (first gas sensor) 66 described later is provided through the hole section 52, a gap between the body unit 2 and the cover unit 3, and the hole section 54 or the hole section 56, to form a closed space. Thereby, during the gas measurement apparatus 1 is in the closed state, a variety of gas components are removed from the closed space in which the semiconductor gas sensor 66 is provided, and it is possible to prevent contamination or degradation of the semiconductor gas sensor 66. The absorbent housing unit 50 may house a gas absorbent such as zeolite, molecular sieve, and silica gel, in place of (or in addition to) activated carbon. Further, the absorbent housing unit 50 can be connected to the space that houses activated carbon and a space in which a second gas sensor 72 described later is provided to form a closed space, and it is possible to prevent contamination or degradation for the second gas sensor 72.

Figure 3:
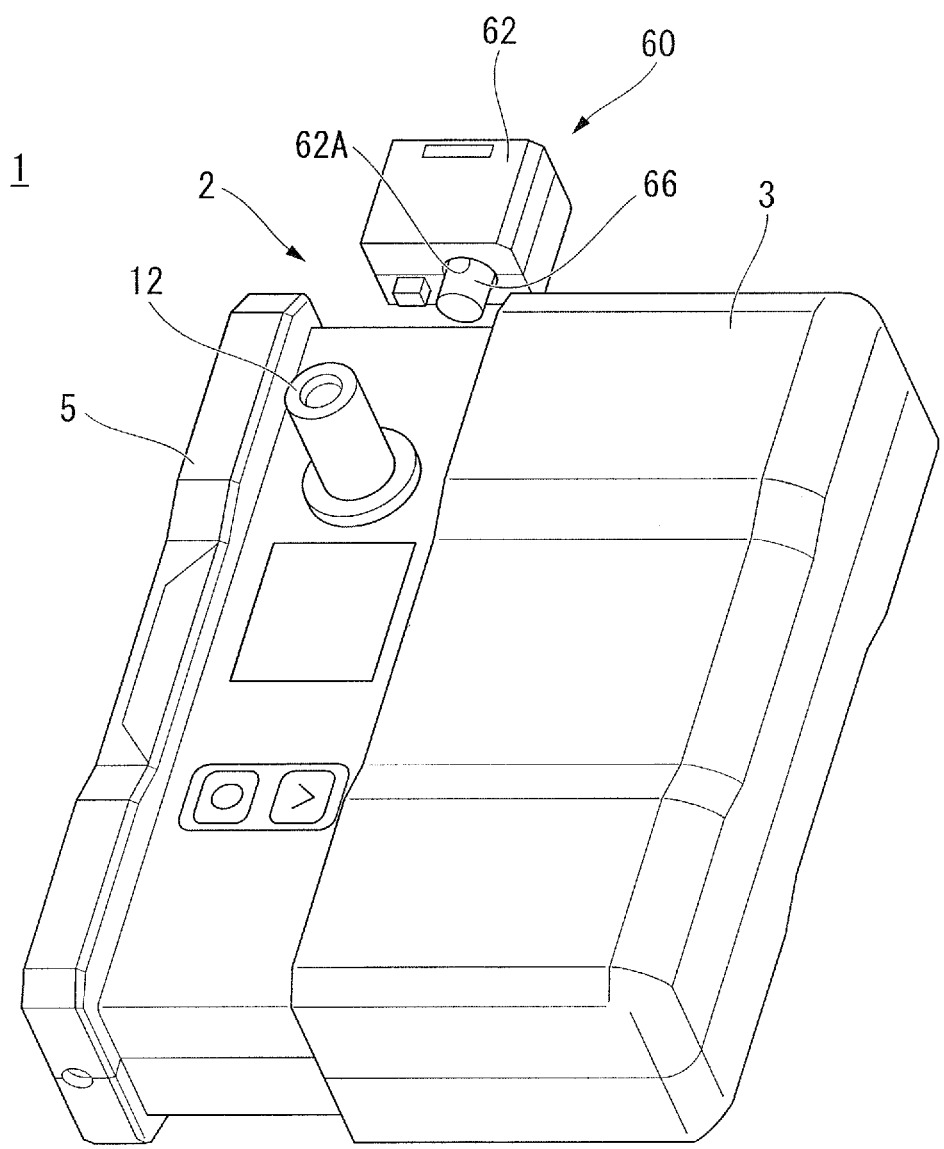
FIG. 3 is an external configuration view of the gas measurement apparatus in a state where a semiconductor gas sensor unit is removed.

A semiconductor gas sensor unit 60 attachable to and detachable from the body unit 2 (replaceable) is attached to the gas measurement apparatus 1. FIG. 3 is an external configuration view of the gas measurement apparatus 1 in a state where the semiconductor gas sensor unit 60 is removed. The semiconductor gas sensor unit 60 houses a sensor circuit board and an electronic component (for example, storage component), in addition to the semiconductor gas sensor 66, within a housing 62 capable of fitting to the body unit 2. The semiconductor gas sensor 66 is provided such that a detection surface protrudes outward of the housing 62 through the hole section 62A provided on the housing 62. Tin oxide ($SnO_2$) or the like is formed on the detection surface of the semiconductor gas sensor 66, and when a detection target gas such as acetone or other interference gas comes into contact with the detection surface, the electric resistance decreases. The semiconductor gas sensor 66 is provided with a heater and an electrode. The semiconductor gas sensor 66 detects the concentration of the detection target gas based on the decrease of the electrical resistance in the detection surface.

The breath of the user includes various types of gases such as ketone body, ethanol, acetaldehyde, carbon monoxide, ammonia, hydrogen, hydrogen sulfide, nitric monoxide, carbon dioxide, and the like. The semiconductor gas sensor 66 detects the concentration of an intended gas and the concentration of an interference gas. The semiconductor gas sensor 66 shows, for example, a high sensitivity with respect to acetone as a type of ketone body. Acetone is a byproduct of lipid metabolism, and the concentration of acetone in the breath is an index value representing the amount of lipid metabolism. When carbohydrate energy is sufficiently present in the body, fat is not burned, and therefore the concentration of acetone in the breath is low. When carbohydrate energy is insufficient in the body, fat is burned, and therefore the concentration of acetone in the breath is high.

The surface of the body unit 2, the cover unit 3, and the housing of the semiconductor gas sensor unit 60 are formed, for example, an acrylonitrile butadiene styrene (ABS) resin, polycarbonate, and the like. The member 6 is, for example, an elastic member such as a rubber (for example, a silicon rubber) and an elastomer. The surface of the display unit 20 is formed, for example, by an acrylonitrile styrene (AS) resin, an acrylic resin, or the like. The button unit of the operation unit 30 is formed by an ABS resin, silicon rubber, and the like.

Figure 4:
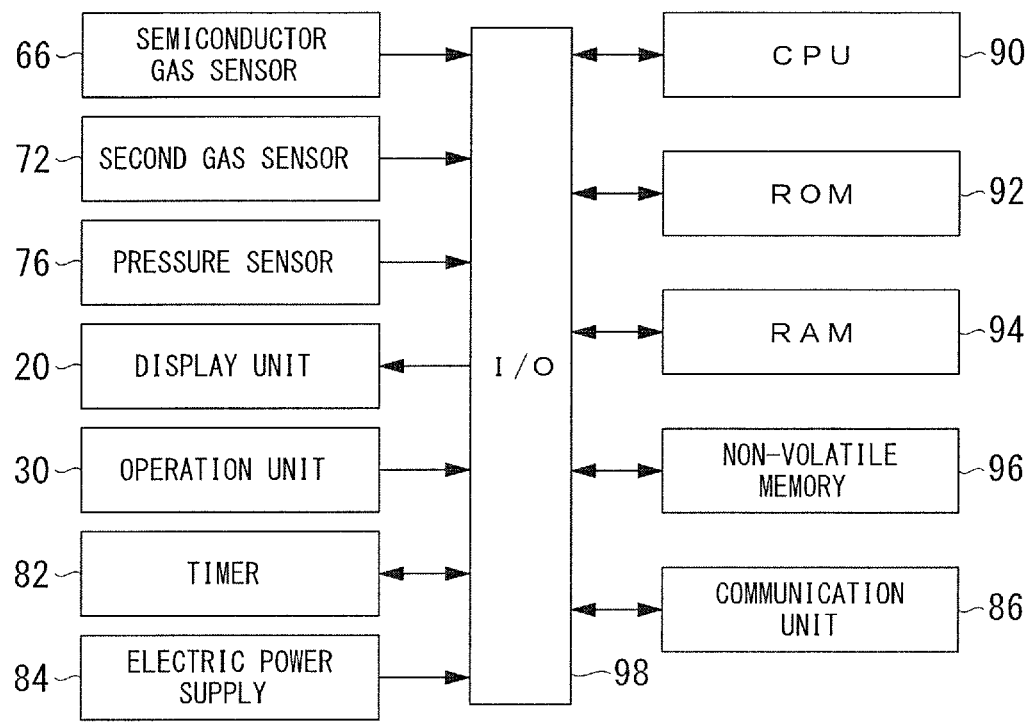
FIG. 4 is a configuration view of a control system of the gas measurement apparatus.

FIG. 4 is a configuration view of a control system of the gas measurement apparatus 1. The gas measurement apparatus 1 includes a second gas sensor unit 70. The second gas sensor unit 70 includes a second gas sensor 72. The second gas sensor 72 is a sensor having a different sensor lifetime due to at least one or more of contamination and degradation from that of the semiconductor gas sensor 66 and detects the concentration of an interference gas. The second gas sensor 72 detects the concentration of a predetermined interference gas, for example, of ethanol, carbon monoxide, ammonia, hydrogen, hydrogen sulfide, nitric monoxide, carbon dioxide, and the like included in an environment or a living body. When a user's breath is delivered to the delivery port 10, the breath is introduced into the inside of the second gas sensor 72 through a pipe and a tube. The gas measurement apparatus 1 determines, for example, whether or not a pressure sensor 76 that measures the pressure of a space inside the gas measurement apparatus 1 connected to the delivery port 10 detects a pressure equal to or greater than a reference value and detects (determines) that the breath is delivered when a pressure equal to or greater than the reference value is detected. When the gas measurement apparatus 1 detects that the breath has been delivered, the gas measurement apparatus 1 causes the second gas sensor 72 to detect the concentration of an interference gas.

The gas measurement apparatus 1 includes a timer 82, an electric power supply 84, a communication unit 86, a central processing unit (CPU) 90, a read only memory (ROM) 92, a random access memory (RAM) 94, a non-volatile memory 96, and the like, in addition to the above-described configurations. The configuration elements are communicatably connected through an I/O 98 to one another. The timer 82, for example, outputs an alarm or measures time when a set time elapses. The electric power supply 84 supplies electricity to each unit from a battery or an external electric power supply. The communication unit 86 performs communication with an external apparatus with a wired or wireless manner.

Figure 5:
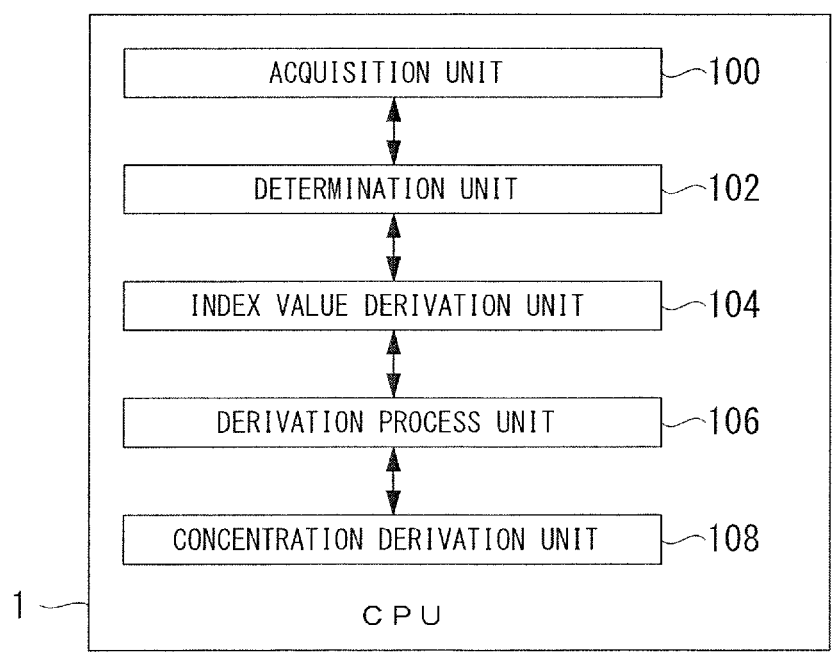
FIG. 5 is a functional block diagram of the gas measurement apparatus.

The CPU 90 (circuitry, circuit) controls each unit of the gas measurement apparatus 1. FIG. 5 is a functional block diagram of the gas measurement apparatus 1. The gas measurement apparatus 1 includes an acquisition unit 100, a determination unit 102, an index value derivation unit 104, a derivation process unit 106, and a concentration derivation unit 108. The derivation process unit 106 and the concentration derivation unit 108 represent an example of a "process unit". The functional units perform a process of determining the measurement result of the gas measurement apparatus 1, for example, in consideration of both a detection value of the semiconductor gas sensor 66 and a detection value of the second gas sensor 72. Detailed functions of the functional units will be described later.

The ROM 92 stores a program executed by the CPU 90 and the like. The RAM 94 functions as a working memory when the CPU 90 performs a process. The non-volatile memory 96 stores the program executed by the CPU 90, data of the user maintained by the gas measurement apparatus 1, and the like. The program executed by the CPU 90, data of the user maintained by the gas measurement apparatus 1, and the like may be provided via a storage medium such as a memory card or may be acquired from an external server apparatus (not shown). The determination unit 102, the index value derivation unit 104, the derivation process unit 106, and the concentration derivation unit 108 of the functional units shown in FIG. 5 are software functional units that function by the CPU 90 executing the program. Further, part or all of the functional units may be hardware functional units such as large scale integration (LSI) or application specific integrated circuit (ASIC).

The acquisition unit 100 causes, for example, the semiconductor gas sensor 66 and the second gas sensor 72 to detect a gas in an environment or in a user's breath at a variety of timings described later.

The determination unit 102, for example, compares two or more detection values detected by the semiconductor gas sensor 66, or compares a detection value detected by the semiconductor gas sensor 66 and a reference value set in advance to determine whether or not the semiconductor gas sensor 66 is contaminated or degraded. Further, the determination unit 102 causes the display unit 20 to display an image indicating a determination result.

The index value derivation unit 104 derives "index Rair" that is an index value used to adjust the detection value of the semiconductor gas sensor 66 and stores the derivation result in the RAM 94, for example, based on the detection value of the second gas sensor 72 in an air in an environment.

The derivation process unit 106 derives the concentration of an intended gas, for example, based on the detection value of the semiconductor gas sensor 66 and the index Rair and calculates the concentration of an interference gas from the detection value of the second gas sensor 72.

The concentration derivation unit 108 determines the measurement result of the gas measurement apparatus 1, for example, in consideration of both the detection value of the semiconductor gas sensor 66 and the detection value of the second gas sensor 72.

Figure 6:
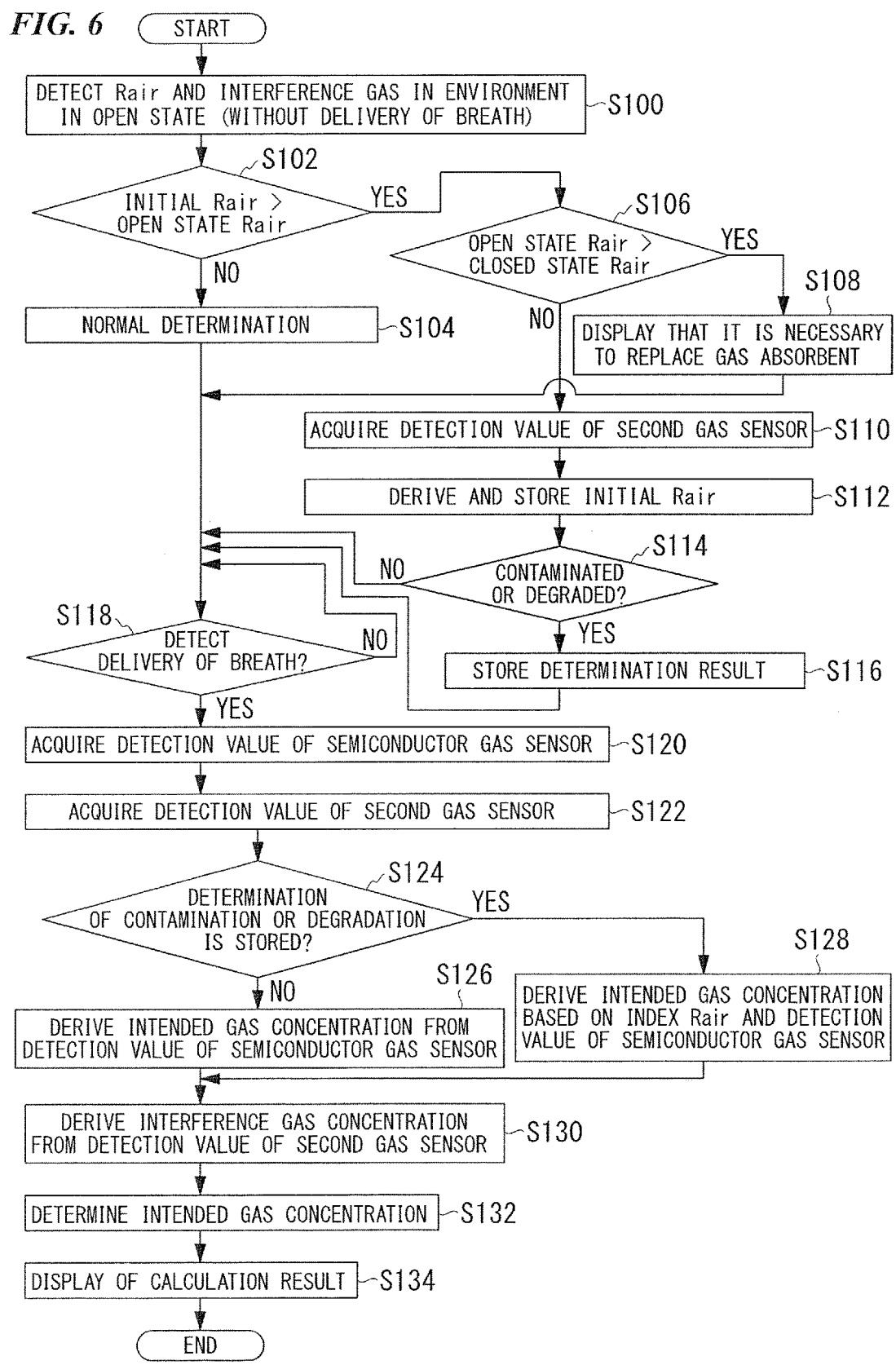
FIG. 6 is a flowchart showing the flow of a determination process of contamination or degradation executed by the gas measurement apparatus.

FIG. 6 is a flowchart showing the flow of the determination process of contamination or degradation executed by the gas measurement apparatus 1. First, when the cover unit 3 of the gas measurement apparatus 1 is operated by a user to be in an open state from a closed state, the acquisition unit 100 instructs the semiconductor gas sensor 66 and the second gas sensor 72 to perform detection with respect to an air in an environment (without delivery of the breath) and acquires the detection value that is detected (step S100). Hereinafter, the detection value of the semiconductor gas sensor 66 is referred to as "Rair", and the detection value of the semiconductor gas sensor 66 in the open state of the gas measurement apparatus 1 is referred to as "open state Rair". The detection result detected by each sensor is stored, for example, in the RAM 94. The detection operation with respect to the air in the environment for determining contamination or degradation may be performed, for example, when the user operates a predetermined button or the like provided on the operation unit 30.

The detection value of the semiconductor gas sensor 66 represents, for example, a lower value as the concentration of the detection target gas of the semiconductor gas sensor 66 is higher. On the other hand, the detection value of the second gas sensor 72 represents a higher value as the concentration of the detection target gas of the second gas sensor 72 is higher. A state where the semiconductor gas sensor 66 is contaminated or degraded is a state where the semiconductor gas sensor 66 outputs a low value (that is, detects that the detection target gas is a high concentration) although the concentration of the detection target gas is low.

Next, the determination unit 102 determines whether or not "initial Rair" exceeds the open state Rair detected in step S100 (step S102). The initial Rair is a reference value that is determined, for example, such that a value measured when the semiconductor gas sensor 66 is not contaminated or degraded such as a factory default is a reference. The initial Rair may be set, for example, to a value that is smaller to some extent than the value measured when the semiconductor gas sensor 66 is not contaminated or degraded. This is because, if the value measured when the semiconductor gas sensor 66 is not contaminated or degraded is set to the initial Rair as is, the determination in step S102 always becomes positive determination due to slight contamination or degradation. Further, the determination unit 102 may determine whether or not the initial Rair exceeds "closed state Rair". In this case, in step S100, the closed state Rair is detected. The initial Rair is stored, for example, in the non-volatile memory 96 in advance.

When the initial Rair is equal to or less than the open state Rair detected in step S100, the determination unit 102 determines that the gas measurement apparatus 1 is normal (the gas measurement apparatus 1 is not contaminated or degraded) (step S104).

On the other hand, when the initial Rair exceeds the open state Rair detected in step S100, the determination unit 102 determines whether or not the open state Rair exceeds Rair (hereinafter, referred to as the closed state Rair) when the gas measurement apparatus 1 is in the closed state (step S106). The closed state Rair is a detection value of the semiconductor gas sensor 66 detected when the gas measurement apparatus 1 is in the closed state (preferably, when a sufficient time has elapsed since the gas measurement apparatus 1 is made to be in the closed state). As the closed state Rair, closed state Rair acquired in step S200 in the process of FIG. 11 described later may be used, or closed state Rair detected in other situations may be used.

When the open state Rair exceeds the closed state Rair, the determination unit 102 causes the display unit 20 to display an image indicating that it is necessary to replace a gas absorbent such as activated carbon housed inside of the absorbent housing unit 50 (step S108). This is because it is estimated that the gas absorbent does not sufficiently work since, although the detection value of the semiconductor gas sensor 66 should be increased according to the function of the gas absorbent when the gas measurement apparatus 1 is in the closed state, the detection value of the semiconductor gas sensor 66 indicates an opposite tendency.

When the open state Rair is equal to or less than the closed state Rair, the index value derivation unit 104 reads out from, for example, the RAM 94 and acquires the detection value of the second gas sensor 72 (step S110).

Next, the index value derivation unit 104 derives index Rair that is an index value used to adjust the detection value of the semiconductor gas sensor 66 and stores the derivation result in the RAM 94 based on the detection value of the second gas sensor 72 in an air in an environment (step S112). The index value derivation unit 104 derives the index Rair, for example, based on Expression (1). In Expression (1), k1 represents a coefficient, k2 represents an intercept, and an optimum value obtained in advance according to experiments or the like is used. Further, Vs is a detection value of the second gas sensor 72, and $\int Vs$ is a time integral value, in a predetermined time, of the detection value of the second gas sensor 72 in an air in an environment. In place of Expression (1), the index Rair may be derived by a calculation using a polynomial expression of two orders or more using $\int Vs$ and an inverse number, an index number, a logarithm, or the like of $\int Vs$. Alternatively, the index Rair may be derived by a map using $\int Vs$ as a coordinate or the like.

Further, a parameter (coefficient k1 as an example) for deriving the index Rair may be adjusted depending on the gender, age, and build of the user. Further, when a discrete value is acquired by sampling, the time integral value can be obtained by summating sampling values.

$$\text{index Rair} = k1 \times \int Vs + k2 \quad (1)$$

The index value derivation unit 104 may store table data based on a correspondence relationship between the peak value of the detection value (Vs) of the second gas sensor 72 obtained by experiments or the like in advance and the integral value of the second gas sensor 72 in the non-volatile memory 96 and the like and may derive the integral value based on the table data.

Next, the determination unit 102 determines whether or not the semiconductor gas sensor 66 is contaminated or degraded (step S114). The determination unit 102 determines that the semiconductor gas sensor 66 is contaminated or degraded, for example, when the open state Rair detected by the semiconductor gas sensor 66 is lower than the index Rair derived based on Expression (1) described above by a predetermined value or more. When it is determined that the semiconductor gas sensor 66 is not contaminated or degraded, the process proceeds to step S118. When it is determined that the semiconductor gas sensor 66 is contaminated or degraded, the determination unit 102 stores the determination result and the content of process in the RAM 94 (step S116).

Figure 7:
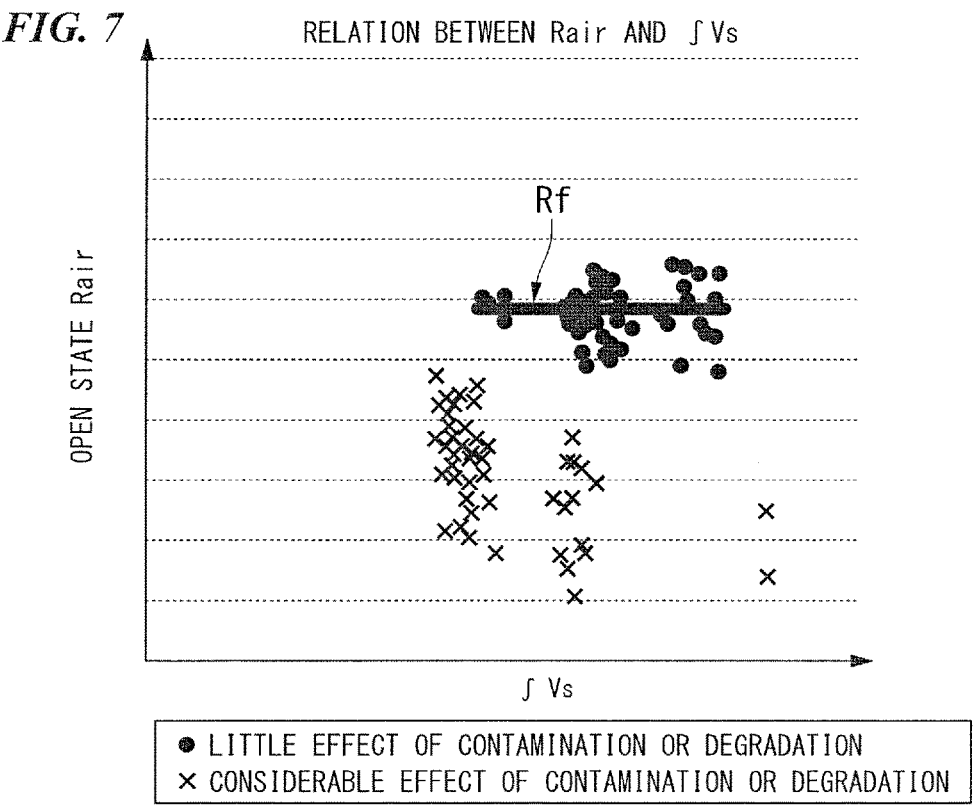
FIG. 7 is a view showing a relation between a detection value detected by a semiconductor gas sensor and a detection value detected by a second gas sensor in a certain environment.

FIG. 7 is a view showing a relation between a detection value detected by the semiconductor gas sensor 66 and a detection value detected by the second gas sensor 72 in a certain environment. The vertical axis of FIG. 7 represents the open state Rair that is a detection value of the semiconductor gas sensor 66. The horizontal axis of FIG. 7 represents the time integral value of the detection value Vs of the second gas sensor 72. In FIG. 7, "Rf" represents a straight line indicating open state Rair=initial Rair. When the detection value detected by the semiconductor gas sensor 66 in a certain environment represents that there is no effect or little effect of contamination or degradation, as shown by a black circle in FIG. 7, the coordinate that is the combination of the open state Rair and the integral Vs is positioned close to the "Rf". On the other hand, in a state where the semiconductor gas sensor 66 is contaminated or degraded, for example, as shown by "X" in FIG. 7, the coordinate that is the combination of the open state Rair and the integral Vs appears at a position below the "Rf". The determination unit 102 determines whether or not the semiconductor gas sensor 66 is contaminated or degraded by comparison of the open state Rair and the initial Rair.

Figure 8:
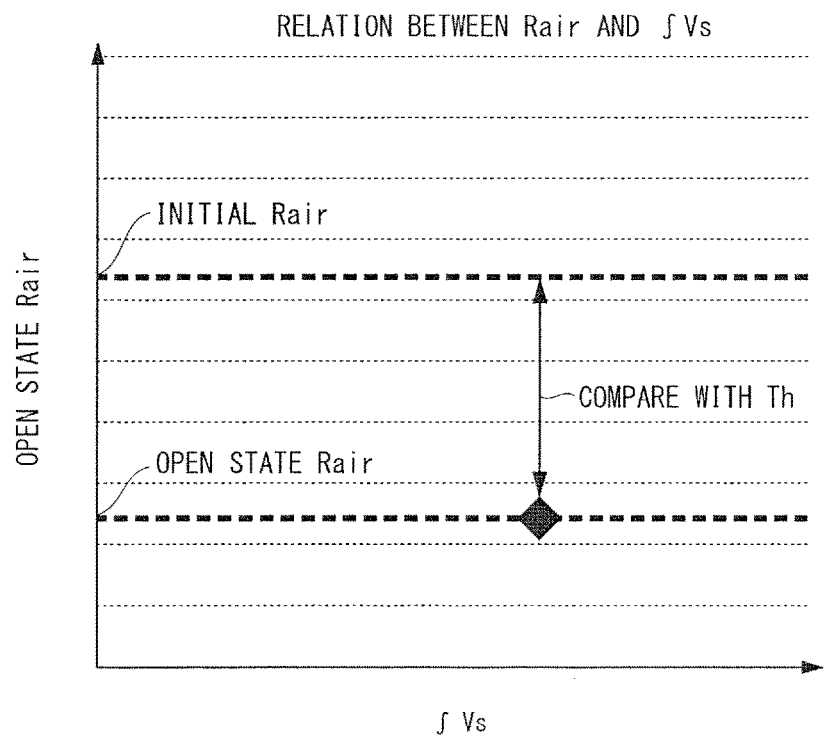
FIG. 8 is a view showing a determination method of contamination or degradation.

FIG. 8 is a view showing a determination method of contamination or degradation. The determination unit 102 determines that the semiconductor gas sensor 66 is contaminated or degraded when the open state Rair is lower by a threshold Th or more than the initial Rair. Further, the determination unit 102 may compare the difference obtained by subtracting the open state Rair from the initial Rair with a plurality of thresholds to thereby determine the state of contamination or degradation in a step-by-step manner.

Figure 9:
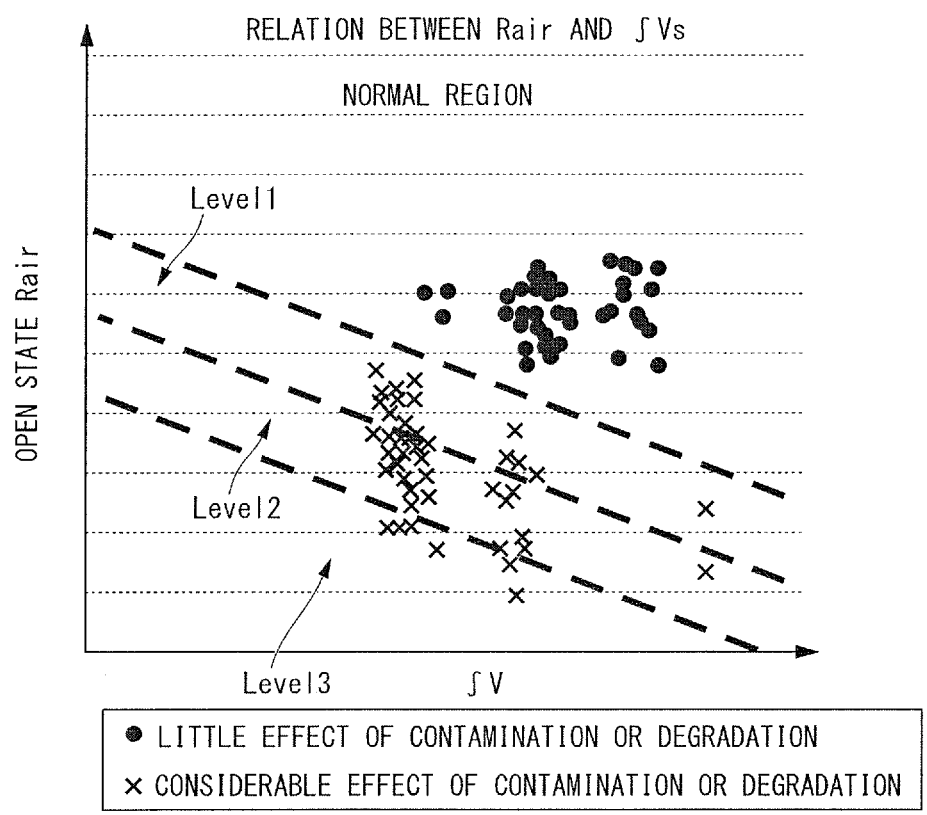
FIG. 9 is a view showing another determination method of contamination or degradation.

FIG. 9 is a view showing another determination method of contamination or degradation. The determination unit 102 may apply the coordinate that is the combination of the open state Rair and the $\int Vs$ to the determination map of contamination or degradation to thereby determine whether or not the semiconductor gas sensor 66 is contaminated or degraded.

As shown in the drawing, in the determination map of contamination or degradation, a "normal region", which is a region that is not contaminated or degraded, a "Level 1 region", which is a region where the level of contamination or degradation is low, a "Level 2 region", which is a region where the level of contamination or degradation is middle, and a "Level 3 region", which is a region where the level of contamination or degradation is high are set, for example, depending on the coordinates. The determination map of contamination or degradation is configured such that the level of contamination or degradation is determined to be low when both the open state Rair and the $\int V$ are high, and the level of contamination or degradation is determined to be high when both the open state Rair and the $\int V$ are low. The region set in the determination map of contamination or degradation is not limited to the example described above; four or more levels of contamination or degradation may be set. Further, when the coordinate is positioned in the "Level 1 region", it may be determined that the semiconductor gas sensor 66 is not contaminated or degraded.

FIG. 6 is described again. The acquisition unit 100 waits until the breath is delivered in the delivery port 10 (step S118). The detection of the breath being delivered is performed, for example, by determining whether or not the pressure sensor 76 provided in the gas measurement apparatus 1 detects a pressure equal to or greater than a reference value.

When a user's breath is delivered to the delivery port 10, the acquisition unit 100 calculates a breath acquisition timing, causes the semiconductor gas sensor 66 and the second gas sensor 72 to perform detection at the calculated breath acquisition timing, and acquires a detection value (step S120, S122). The derivation process unit 106 stores the detection values of the semiconductor gas sensor 66 and the second gas sensor 72 acquired by the acquisition unit 100 in the RAM 94.

Next, the derivation process unit 106 determines whether or not the determination result (refer to step S116) of contamination or degradation with respect to the semiconductor gas sensor 66 is stored in the RAM 94 (step S124). When information indicating that the semiconductor gas sensor 66 is contaminated or degraded is not stored, the derivation process unit 106 derives the concentration of an intended gas from the detection value of the semiconductor gas sensor 66 (step S126). The concentration of the intended gas is calculated, for example, based on Expression (2), by multiplying a detection value Rs of the semiconductor gas sensor 66 when a user's breath is delivered by a coefficient k3 that is an optimum value obtained in advance according to experiments or the like and adding an intercept k4. In place of Expression (2), Conc1 may be derived by a calculation using a polynomial expression of two orders or more using Rs and an inverse number, an index number, a logarithm, or the like of Rs. Alternatively, Conc1 may be derived by a map using Rs as a coordinate. Further, a parameter (coefficient k3 as an example) for deriving Conc1 may be adjusted depending on the gender, age, and build of the user.

$$\text{Conc1} = k3 \times Rs + k4 \quad (2)$$

When information indicating that the semiconductor gas sensor 66 is contaminated or degraded is stored, the derivation process unit 106 derives the concentration of the intended gas based on the detection value of the semiconductor gas sensor 66 and the index Rair (step S128). For example, a measurement result Conc1# of the gas measurement apparatus 1 is derived based on Expression (3) or Expression (4). In Expression (3), k5 represents a coefficient, and an optimum value obtained in advance according to experiments or the like is used for k5. Rs is a detection value of the semiconductor gas sensor 66 when the breath is measured. k6 represents an intercept. In place of Expression (3) and Expression (4), the measurement result Conc1# of the gas measurement apparatus 1 may be derived by a polynomial expression of two orders or more using Rs and index Rair. Alternatively, the measurement result Conc1# of the gas measurement apparatus 1 may be derived by a map using (Rs/index Rair) or Rs/{index Rair+(index Rair−open state Rair)} as a coordinate. Further, a parameter (coefficient k5 as an example) for deriving the measurement result Conc1# of the gas measurement apparatus 1 may be adjusted depending on the gender, age, and build of the user.

$$\text{Conc1#} = k5 \times (Rs/\text{index Rair}) + k6 \quad (3)$$

$$\text{Conc1#} = k5 \times Rs/\{\text{index Rair} + (\text{index Rair} - \text{open state Rair})\} + k6 \quad (4)$$

Next, the derivation process unit 106 calculates the concentration of an interference gas from the detection value of the second gas sensor 72 (step S130). For example, a measurement result Conc2 of the gas measurement apparatus 1 is derived based on Expression (5). In Expression (5), k6 represents a coefficient, and an optimum value obtained in advance according to experiments or the like is used for k6. Rt is a detection value of the second gas sensor 72 when the breath is delivered. k7 represents an intercept. In place of Expression (5), the measurement result Conc2 of the gas measurement apparatus 1 may be derived by a polynomial expression of two orders or more using Rt. Alternatively, the measurement result Conc2 of the gas measurement apparatus 1 may be derived by a map using Rt as a coordinate. Further, a parameter (coefficient k6 as an example) for deriving the measurement result Conc2 of the gas measurement apparatus 1 may be adjusted depending on the gender, age, and build of the user.

$$\text{Conc2} = k6 \times Rt + k7 \quad (5)$$

Next, the concentration derivation unit 108 determines the measurement result of the gas measurement apparatus 1, for example, in consideration of both the detection value of the semiconductor gas sensor 66 and the detection value of the second gas sensor 72 (step S132). The concentration derivation unit 108 derives a measurement result Conc3 of the gas measurement apparatus 1, for example, based on Expression (6) or Expression (7). In Expression (6), C1 represents Conc1 derived from the detection value of the semiconductor gas sensor 66 determined to be not contaminated or degraded derived by Expression (2) described above. In Expression (7), C1# represents Conc1# derived based on the index Rair and the detection value of the semiconductor gas sensor 66 determined to be contaminated or degraded derived by Expression (3) and Expression (4) described above. Further, C2 represents Conc2 derived from the detection value of the second gas sensor 72 derived by Expression (5) described above. k8 represents a coefficient, and an optimum value obtained in advance according to experiments or the like is used for k8. k9 represents a coefficient, and an optimum value obtained in advance according to experiments or the like is used for k9. k9 is set to, for example, a negative value. In place of Expression (6) and Expression (7), the measurement result Conc3 of the gas measurement apparatus 1 may be derived by a polynomial expression of two orders or more using C1 and C2 or using C1# and C2. Alternatively, the measurement result Conc3 of the gas measurement apparatus 1 may be derived by a map using C1 and C2 as coordinates or a map using C1# and C2 as coordinates. Further, a parameter (coefficients k8, k9 as examples) for deriving the measurement result Conc3 of the gas measurement apparatus 1 may be adjusted depending on the gender, age, and build of the user.

$$\text{Conc3} = k8 \times C1 + k9 \times C2 \quad (6)$$

$$\text{Conc3} = k8 \times C1\# + k9 \times C2 \quad (7)$$

The detection value of the semiconductor gas sensor 66 or the second gas sensor 72 may be a voltage value (V), a resistance value (kΩ), a current value (A), or the like. The detection value of the semiconductor gas sensor 66 or the second gas sensor 72 may be an integral value in a period of time from a time when the detection value of the semiconductor sensor 66 or the second gas sensor 72 becomes a certain detection value (for example, a peak value) to a time when the detection value of the semiconductor gas sensor 66 or the second gas sensor 72 returns to a detection value in a steady state.

Then, the concentration derivation unit 108 causes the display unit 20 to display the determined measurement result of the gas measurement apparatus 1 (step S134). When the determination unit 102 determines that the gas measurement apparatus 1 is contaminated or degraded (refer to step S114), the gas measurement apparatus 1 may cause the display unit 20 to display the measurement result along with the level of contamination or degradation. Alternatively, the determination unit 102 may cause the display unit 20 to display an image including a component of the semiconductor gas sensor 66 or an advice such as maintenance based on the determination result of contamination or degradation, or the determination result of the level of contamination or degradation. Thereby, the process of the present flowchart ends.

The process (process relating to determination of contamination or degradation) of step S102, S106, S114, S116, or S124 may be omitted, and the concentration of the intended gas may be derived based on the index Rair for all detection values detected by the semiconductor gas sensor 66. Alternatively, for example, in the process of step S114, the concentration of the intended gas may be derived without using the index Rair when the values of the index Rair and the Rair are within a predetermined value or when the determination result of contamination or degradation is, for example, Level 1 described above.

Figure 10:
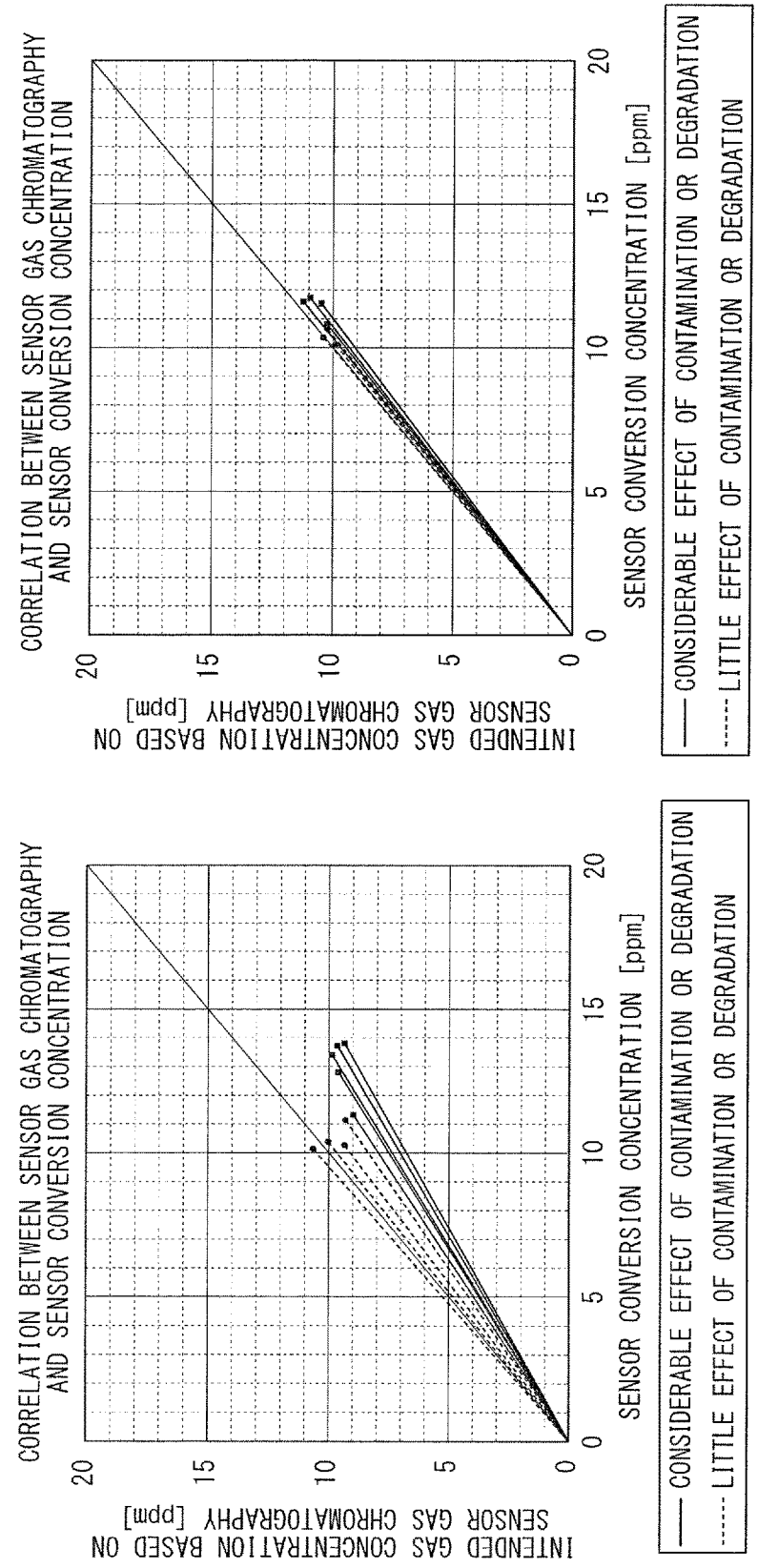
FIG. 10 is a view showing a result of deriving the concentration of an intended gas based on Rair and a result of deriving the concentration of an intended gas based on index Rair.

FIG. 10 is a view showing a result of deriving the concentration of an intended gas based on the Rair and a result of deriving the concentration of an intended gas based on the index Rair. The drawing on the left shows a result of deriving the concentration of the intended gas without using the index Rair. The drawing on the right shows a result of deriving the concentration of the intended gas using the index Rair. The vertical axis of FIG. 10 represents an intended gas concentration [ppm] detected by sensor gas chromatography. The horizontal axis of FIG. 10 represents a concentration [ppm] to which the detection value of the intended gas detected by the gas measurement apparatus 1 is converted by executing the process described above. The solid line in FIG. 10 shows a measurement result of the gas measurement apparatus on which there is considerable effect of contamination or degradation, and the dashed line shows a measurement result of the gas measurement apparatus on which there is no effect or little effect of contamination or degradation. In sensor gas chromatography, since the components included in a gas are separated individually to measure the separated component quantitatively, it is possible to accurately measure each component. As shown in the figure, when the concentration of the intended gas is derived based on the Rair detected by the gas measurement apparatus, the correlation between the detection result of the sensor gas chromatography and the detection result of the gas measurement apparatus is low. Specifically, the correlation between the detection result of the gas measurement apparatus on which there is considerable effect of contamination or degradation and the measurement result of the sensor gas chromatography is low. On the other hand, when the concentration of the intended gas is derived based on the index Rair in the gas measurement apparatus 1, the correlation between the detection result of the sensor gas chromatography and the measurement result of the gas measurement apparatus on which there is considerable effect of contamination or degradation and on which there is no effect or little effect of contamination or degradation is high.

According to the gas measurement apparatus 1 of the first embodiment described above, since the determination unit 102 compares the detection value of the gas sensor acquired in the open state and the detection value of the gas sensor acquired in the closed state to thereby determine the state of the gas sensor, it is possible to accurately determine the state of the gas measurement apparatus 1. Further, the gas measurement apparatus 1 includes: the acquisition unit that acquires the detection value of the first gas sensor (semiconductor gas sensor 66) and the detection value of the second sensor (second gas sensor 72) having a sensor lifetime due to contamination or degradation, which is different from that of the first gas sensor; the index value derivation unit that derives an index value used to adjust the detection value of the first gas sensor based on the detection value acquired from the second sensor; and the process unit that derives the concentration of the intended gas by adjusting the detection value of the first gas sensor using the index value derived by the index value derivation unit. Therefore, it is possible to accurately measure the intended gas.

Second Embodiment

Figure 11:
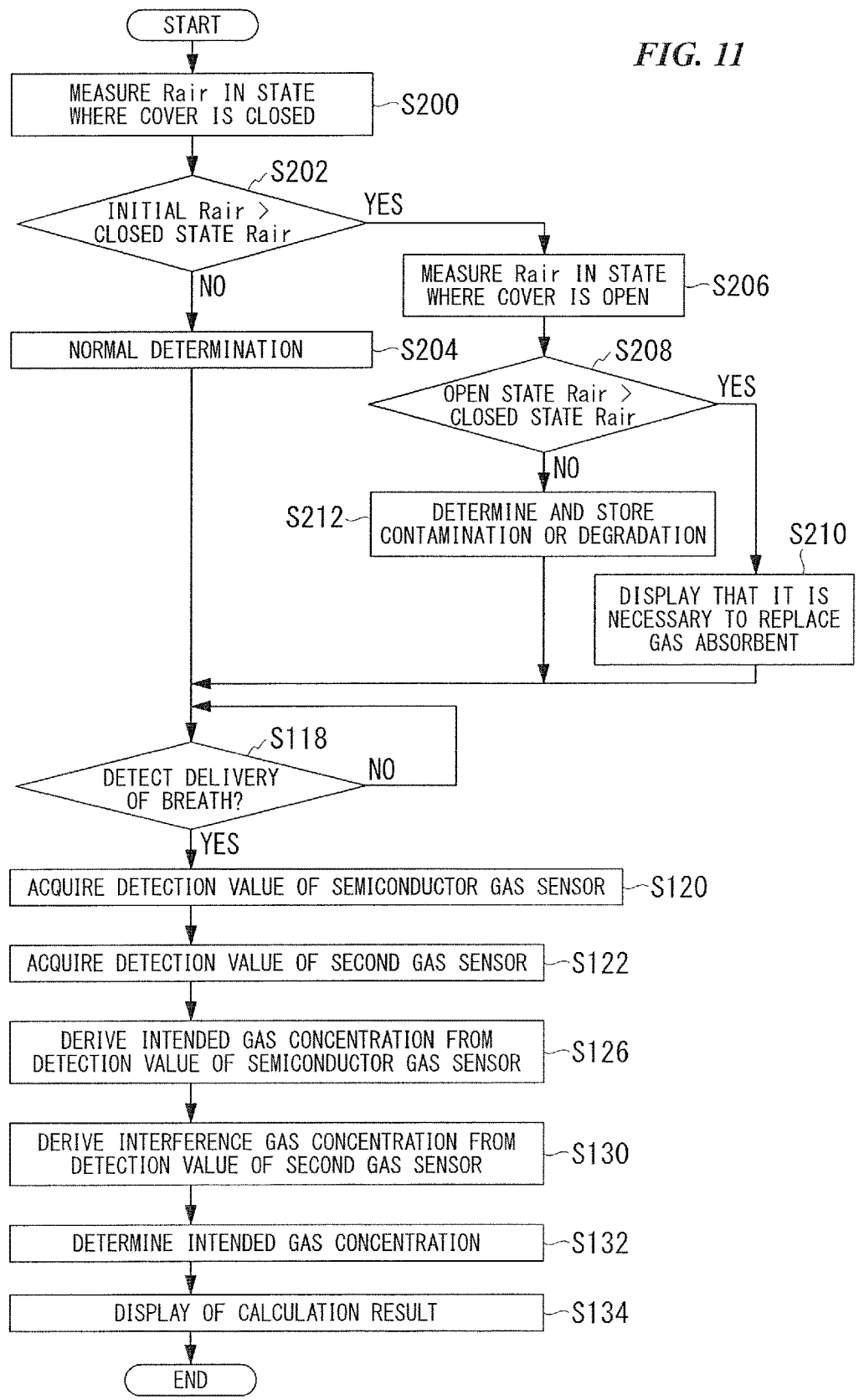
FIG. 11 is a flowchart showing the flow of a process executed by a gas measurement apparatus in a second embodiment.

FIG. 11 is a flowchart showing the flow of a process executed by the gas measurement apparatus 1 in the second embodiment. Description of the process similar to FIG. 6 described above is omitted.

First, when the cover unit 3 of the gas measurement apparatus 1 is operated by a user to be in a closed state from an open state, the acquisition unit 100 instructs the semiconductor gas sensor 66 and the second gas sensor 72 to perform detection with respect to an air in an environment (without delivery of the user's breath) and acquires the detection value that is detected (step S200). The determination unit 102 determines whether or not initial Rair exceeds closed state Rair detected in step S200 (step S202). When the initial Rair is equal to or less than the closed state Rair detected in step S200, the determination unit 102 determines that the gas measurement apparatus 1 is normal (the gas measurement apparatus 1 is not contaminated or degraded) (step S204).

In step S202, the determination unit 102 may determine whether or not the initial Rair exceeds the open state Rair detected in step S200; however, by comparing the initial Rair with the closed state Rair, even when an interference gas is present in an environment, it is possible to appropriately determine whether or not the semiconductor gas sensor 66 is normal according to the function of the gas absorbent.

On the other hand, when the initial Rair exceeds the closed state Rair detected in step S200, and when the cover unit 3 of the gas measurement apparatus 1 is operated by a user to be in a closed state from an open state, the determination unit 102 instructs the acquisition unit 100 such that the semiconductor gas sensor 66 and the second gas sensor 72 perform detection with respect to an air in an environment (without delivery of the user's breath) and acquires the detection value that is detected (step S206). The determination unit 102 determines whether or not the open state Rair detected in step S206 exceeds the closed state Rair detected in step S200 (step S208). When the open state Rair detected in step S206 exceeds the closed state Rair detected in step S200, the determination unit 102 determines that it is necessary to replace the gas absorbent (step S210). When the open state Rair detected in step S206 is equal to or less than the closed state Rair detected in step S200, the determination unit 102 determines that the gas measurement apparatus 1 is contaminated or degraded and stores the determination result in the RAM 94 (step S212). The determination unit 102 may determine that the level of contamination or degradation is Level 3 when the difference between the open state Rair and the closed state Rair is large, determine that the level of contamination or degradation is Level 2 when the difference is middle, and determine that the level of contamination or degradation is Level 1 when the difference is small.

Then, the determination unit 102 causes the display unit 20 to display the determined measurement result of the gas measurement apparatus 1 and display the state of contamination or degradation of the gas measurement apparatus 1, the level of contamination or degradation, or the like (step S134). Thereby, the process of the present flowchart ends. Further, when the second gas sensor 72 is not used, the processes of step S122, step S130, and step S132 in the present flowchart may be omitted. Further, when the intended gas concentration is not calculated, the processes of step S118 to step S134 in the present flowchart may be omitted, and the determination unit 102 may display on the display unit 20 the determination result of contamination or degradation, or indication representing replacement of the gas absorbent.

According to the gas measurement apparatus 1 of the second embodiment described above, the gas measurement apparatus 1 compares an initial detection value, a detection value in the closed state, and a detection value in the open state, and thereby it is possible to determine whether the gas measurement apparatus 1 is in a normal state, whether the gas measurement apparatus 1 is in a state of being contaminated or degraded, or whether or not the gas measurement apparatus 1 is in a state where it is necessary to replace the gas absorbent. Further, when the gas measurement apparatus 1 is in a state of being contaminated or degraded, by displaying the measurement result along with the level of contamination or degradation, it is possible to provide the measurement result to the user and provide accuracy of the measurement result.

The detection target gas of the second gas sensor 72 may be ethanol, nitric monoxide, ammonia, hydrogen, hydrogen sulfide, carbon monoxide, or the like. Further, the following symptoms may be evaluated based on the detection value detected by the semiconductor gas sensor 66 and the detection value of a predetermined gas detected by the second gas sensor 72. When the detection target gas of the second gas sensor 72 is, for example, nitric monoxide, it is possible to evaluate smoking, bronchial asthma, airway infection, pulmonary hypertension, or the like. When the detection target gas is, for example, ammonia, it is possible to detect hepatic encephalopathy, congenital enzymopathy of the urea cycle, *H. pylori* infection, and the like. When the detection target gas is, for example, hydrogen, it is possible to evaluate overgrowth of intestinal anaerobic bacteria, maldigestion syndrome, indigestible glucose, intestinal flora and the like. When the detection target gas is, for example, hydrogen sulfide, it is possible to evaluate periodontal disease. When the detection target gas is, for example, carbon monoxide, it is possible to evaluate gas contamination, smoking, and the like.

Figure 12:
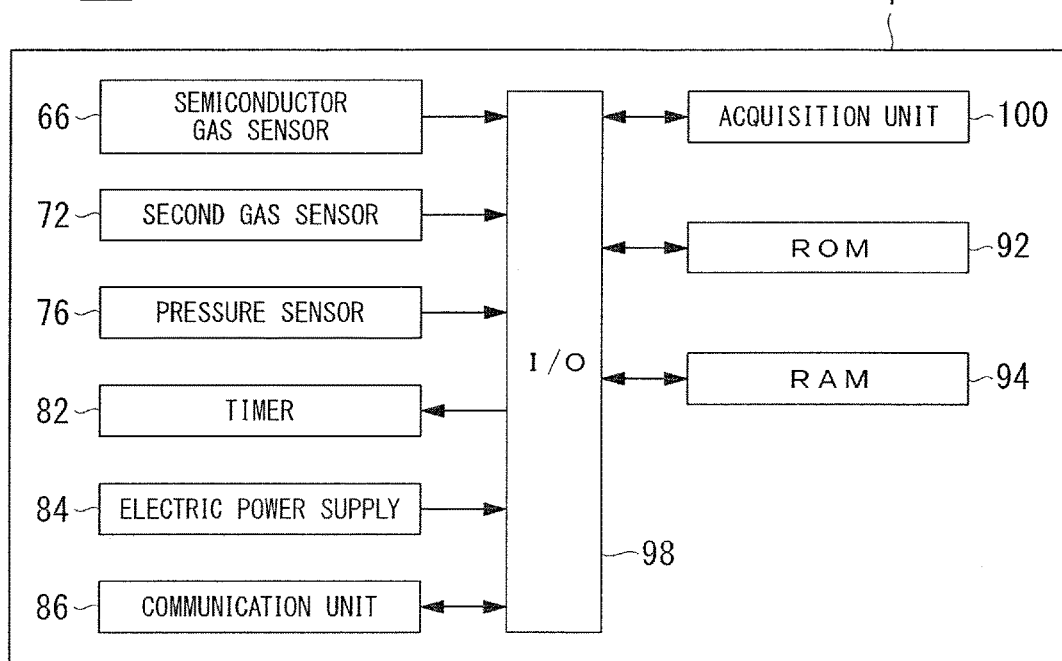
FIG. 12 is a view showing a configuration example of a gas measurement system in a case where part of a gas measurement apparatus is configured as a separate apparatus capable of communicating with the gas measurement apparatus.
Figure 12:
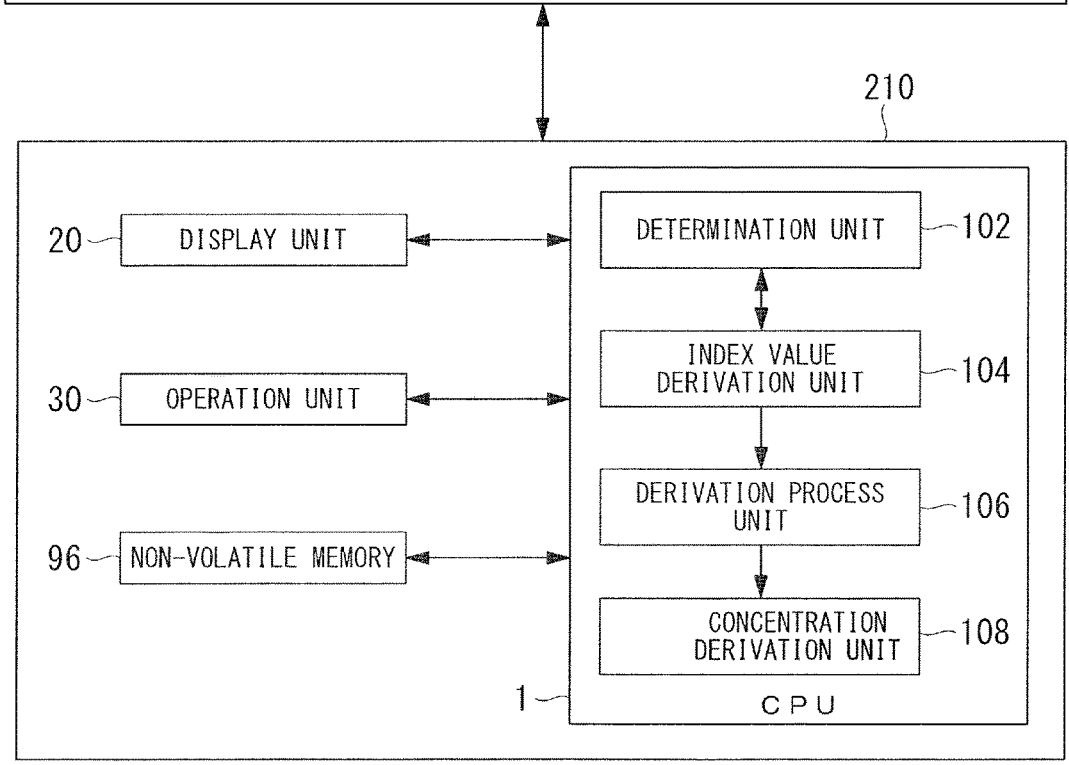

The above embodiment is described using an example in which the gas measurement apparatus 1 includes, in one apparatus, the display unit 20, the operation unit 30, and each functional unit for adjusting the detection value of the semiconductor gas sensor 66; however, part or all of the display unit 20, the operation unit 30, each functional unit, and the non-volatile memory 96 may be a separate apparatus capable of communicating with the gas measurement apparatus including the semiconductor gas sensor 66. FIG. 12 is a view showing a configuration example of a gas measurement system 200 in a case where part of the gas measurement apparatus is configured as a separate apparatus capable of communicating with the gas measurement apparatus 1. A terminal apparatus 210 includes the display unit 20, the operation unit 30, the determination unit 102, the index value derivation unit 104, the derivation process unit 106, the concentration derivation unit 108, and the non-volatile memory 96 described above. The gas measurement apparatus 1 transmits information such as the detection value of each sensor to the terminal apparatus 210 through the communication unit 86. The terminal apparatus 210 performs a process similar to that of the gas measurement apparatus 1 in the above embodiment to obtain a measurement result.

Although the embodiment of the invention has been described, the invention is not limited to the above-described embodiment, and a variety of modification and substitution can be added without departing from the scope of the invention.

The invention claimed is:

1. A gas measurement apparatus that includes a gas sensor and is capable of being in any one of an open state in which the gas sensor is connected to an outside air and a closed state in which the gas sensor is cut off from an outside air, the gas measurement apparatus comprising:
an acquisition unit;
a determination unit,
a second gas sensor having a sensor lifetime due to at least one or more of contamination and degradation, the sensor lifetime being different from a sensor lifetime of the gas sensor; and
an index value derivation unit that derives an index value based on a detection value acquired from the second gas sensor,
wherein
the acquisition unit acquires a detection value of the gas sensor in the open state and a detection value of the gas sensor in the closed state,
the acquisition unit further acquires the detection value of the second gas sensor,
the determination unit compares the detection value of the gas sensor acquired in the open state and the detection value of the gas sensor acquired in the closed state to thereby determine the state of the gas sensor, and
the determination unit determines the state of the gas sensor using the index value derived by the index value derivation unit.

2. The gas measurement apparatus according to claim 1, wherein
the determination unit further compares the detection value of the gas sensor acquired in the open state or the detection value of the gas sensor acquired in the closed state with a reference value to thereby determine the state of the gas sensor.

3. The gas measurement apparatus according to claim 1, comprising:
an absorbent housing unit that houses a gas absorbent, wherein
at least in the closed state, a space in which the gas sensor is provided and the inside of the absorbent housing unit are connected to each other.

4. The gas measurement apparatus according to claim 3, wherein
the determination unit determines that there is an abnormality in the gas absorbent when it is determined that the detection value of the gas sensor acquired in the open state exceeds the detection value of the gas sensor acquired in the closed state.

5. The gas measurement apparatus according to claim 1, wherein
the index value derivation unit derives an index value used to adjust a detection value of the gas sensor based on a detection value of a gas detected by the second gas sensor in a case where a user's breath is not delivered, and
the gas measurement apparatus comprises a process unit that adjusts the detection value of the gas sensor using the index value derived by the index value derivation unit to thereby derive the concentration of an intended gas.

6. The gas measurement apparatus according to claim 1, wherein
the index value derivation unit derives the index value based on a time integral value or a peak value of the detection value acquired from the second gas sensor.

7. The gas measurement apparatus according to claim 1, wherein
the determination unit determines that there is an abnormality in the gas sensor when it is determined that the detection value of the gas sensor acquired in the open state is equal to or less than the detection value of the gas sensor acquired in the closed state.

8. The gas measurement apparatus according to claim 7, wherein
the determination unit determines an abnormality level of the gas sensor by a plurality of steps based on the detection value of the gas sensor.

9. The gas measurement apparatus according to claim 1, wherein
the determination unit causes a display unit to display an image representing the result of the determination.

10. The gas measurement apparatus according to claim 1, comprising:
a delivery port to which a gas is delivered; and
a cover unit, by being operated, capable of being in any one of an open state in which the gas sensor is connected to an outside air and a closed state in which the gas sensor is cut off from an outside air.

11. A gas measurement system, comprising:
the gas measurement apparatus according to claim 1, the gas measurement apparatus transmitting the detection value detected by the gas sensor to a terminal apparatus; and
the terminal apparatus that acquires the transmitted detection value.

12. A gas measurement method comprising:
by way of a gas measurement apparatus that includes: a gas sensor; and a second gas sensor having a sensor lifetime due to at least one or more of contamination and degradation, the sensor lifetime being different from a sensor lifetime of the gas sensor, and that is capable of being in any one of an open state in which the gas sensor is connected to an outside air and a closed state in which the gas sensor is cut off from an outside air,
acquiring a detection value of the gas sensor in the open state and a detection value of the gas sensor in the closed state;
further acquiring the detection value of the second gas sensor;
deriving an index value based on a detection value acquired from the second gas sensor;
comparing the detection value of the gas sensor acquired in the open state and the detection value of the gas sensor acquired in the closed state to thereby determine the state of the gas sensor; and
determining the state of the gas sensor using the derived index value.

13. A non-transitory computer-readable recording medium including a gas measurement program which causes a control computer of a gas measurement apparatus that includes: a gas sensor; and a second gas sensor having a sensor lifetime due to at least one or more of contamination and degradation, the sensor lifetime being different from a sensor lifetime of the gas sensor, and that is capable of being in any one of an open state in which the gas sensor is connected to an outside air and a closed state in which the gas sensor is cut off from an outside air, to:
acquire a detection value of the gas sensor in the open state and a detection value of the gas sensor in the closed state;
further acquire the detection value of the second gas sensor;
derive an index value based on a detection value acquired from the second gas sensor;
compare the detection value of the gas sensor acquired in the open state and the detection value of the gas sensor acquired in the closed state to thereby determine the state of the gas sensor; and
determine the state of the gas sensor using the derived index value.

* * * * *